US008821762B2

(12) United States Patent
Tierney et al.

(10) Patent No.: US 8,821,762 B2
(45) Date of Patent: Sep. 2, 2014

(54) ANTHRA[2,3-B]BENZO[D]THIOPHENE DERIVATIVES AND THEIR USE AS ORGANIC SEMICONDUCTORS

(75) Inventors: Steven Tierney, Southampton (GB); Changsheng Wang, Durham (GB); William Mitchell, Chandler's Ford (GB)

(73) Assignee: Merck Patent GmbH, Darmstadt (DE)

( * ) Notice: Subject to any disclaimer, the term of this patent is extended or adjusted under 35 U.S.C. 154(b) by 699 days.

(21) Appl. No.: 13/140,493

(22) PCT Filed: Nov. 27, 2009

(86) PCT No.: PCT/EP2009/008460
§ 371 (c)(1),
(2), (4) Date: Jun. 17, 2011

(87) PCT Pub. No.: WO2010/069457
PCT Pub. Date: Jun. 24, 2010

(65) Prior Publication Data
US 2011/0248220 A1     Oct. 13, 2011

(30) Foreign Application Priority Data

Dec. 18, 2008  (EP) ..................................... 08022056

(51) Int. Cl.
*H01B 1/12*      (2006.01)
*H01L 29/08*     (2006.01)
*C07D 495/04*    (2006.01)
*C07D 513/04*    (2006.01)
*H01L 51/00*     (2006.01)

(52) U.S. Cl.
CPC ........... *C07D 495/04* (2013.01); *C07D 513/04* (2013.01); *H01L 51/0068* (2013.01); *H01L 51/0094* (2013.01)
USPC .............................................. 252/500; 257/40

(58) Field of Classification Search
None
See application file for complete search history.

(56) References Cited

U.S. PATENT DOCUMENTS

| 8,101,776 B2 | 1/2012 | Berens et al. |
| 2009/0299070 A1 | 12/2009 | Berens et al. |
| 2011/0057182 A1* | 3/2011 | Lee et al. ......................... 257/40 |

FOREIGN PATENT DOCUMENTS

WO     2007068618 A1    6/2007

OTHER PUBLICATIONS

Du et al. "Anthra[2,3-b]benzo[d]thiophene : An Air-Stable Asymmetric Organic Semiconductor with High Mobility at Room Temperature". (Chemistry of Materials) pp. 4188-4190, vol. 20, Jun. 6, 2008.
Anthony et al. "A Road Map to Stable, Soluble, Easily Crystallized Pentacene Derivatives". (Organic Letters) pp. 15-18, vol. 4, No. 1, Dec. 15, 2001.
World IP Organization. "International Search Report". PCT/EP2009/008460. Applicant: Merck Patent GMBH, Mailed: Mar. 5, 2010.
Search Report related to corresponding Taiwanese Patent Application No. 098143404 dated Feb. 10, 2014.

* cited by examiner

*Primary Examiner* — Harold Pyon
*Assistant Examiner* — Jaison Thomas
(74) *Attorney, Agent, or Firm* — Millen, White, Zelano & Branigan, P.C.

(57) ABSTRACT

The invention relates to novel anthra[2,3-b]benzo[d]thiophene derivatives, methods of their preparation, their use as semiconductors in organic electronic (OE) devices, and to OE devices comprising these derivatives.

17 Claims, 2 Drawing Sheets

ANTHRA[2,3-B]BENZO[D]THIOPHENE DERIVATIVES AND THEIR USE AS ORGANIC SEMICONDUCTORS

FIELD OF THE INVENTION

The invention relates to novel anthra[2,3-b]benzo[d]thiophene derivatives, methods of their preparation, their use as semiconductors in organic electronic (OE) devices, and to OE devices comprising these derivatives.

BACKGROUND AND PRIOR ART

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), photodetectors, organic photovoltaic (OPV) cells, sensors, memory elements and logic circuits to name just a few. The organic semiconducting materials are typically present in the electronic device in the form of a thin layer, for example less than 1 micron thick.

The performance of OFET devices is principally based upon the charge carrier mobility of the semiconducting material and the current on/off ratio, so the ideal semiconductor should have a low conductivity in the off state, combined with a high charge carrier mobility ($>1\times10^{-3}$ cm$^2$ V$^{-1}$ s$^{-1}$). In addition, it is important that the semiconducting material is relatively stable to oxidation i.e. it has a high ionisation potential, as oxidation leads to reduced device performance. Further requirements for the semiconducting material are a good processability, especially for large-scale production of thin layers and desired patterns, and high stability, film uniformity and integrity of the organic semiconductor layer.

in prior art various materials have been proposed for use as OSCs in OFETs, including small molecules like for example pentacene, and polymers like for example polyhexylthiophene.

A promising class of conjugated small molecule semiconductors has been based upon the pentacene unit.[1] When deposited as a thin film by vacuum deposition, it was shown to have carrier mobilities in excess of 1 cm$^2$ V$^{-1}$ s$^{-1}$ with very high current on/off ratios greater than 10$^6$.[2] However, vacuum deposition is an expensive processing technique that is unsuitable for the fabrication of large-area films. Initial device fabrication was improved by adding solubilising groups, such as trialkylsilylethynyl, allowing mobilities >0.1 cm$^2$V$^{-1}$ s$^{-1}$ [3]. It has also been reported that adding further substituents to the pentacene core unit can improve its semiconducting performance in field-effect transistor (FET) devices.[1]

However, the OSC materials of prior art, and devices comprising them, which have been investigated so far, do still have several drawbacks, and their properties, especially the solubility, processibility, charge-carrier mobility, on/off ratio and stability still leave room for further improvement.

Therefore, there is still a need for OSC materials that show good electronic properties, especially high charge carrier mobility, and good processability, especially a high solubility in organic solvents. Moreover, for use in OFETs there is a need for OSC materials that allow improved charge injection into the semiconducting layer from the source-drain electrodes. For use in OPV cells, there is a need for OSC materials having a low bandgap, which enable improved light harvesting by the photoactive layer and can lead to higher cell efficiencies.

It was an aim of the present invention to provide compounds for use as organic semiconducting materials that do not have the drawbacks of prior art materials as described above, and do especially show good processibility, good solubility in organic solvents and high charge carrier mobility. Another aim of the invention was to extend the pool of organic semiconducting materials available to the expert. Other aims of the present invention are immediately evident to the expert from the following detailed description.

It was found that these aims can be achieved by providing compounds as claimed in the present invention. In particular, the inventors of this invention have found that compounds derived from anthra[2,3-b]benzo[d]thiophene, which is disubstituted by ethynyl groups in 7- and 12-position, are suitable as semiconductors, exhibit very good solubility in most organic solvents, and show high performance when used as semiconducting layer in electronic devices like OFETs. It was found that OFET devices comprising such compounds as semiconductors show good mobility and on/off ratio values and can easily be prepared using solution deposition fabrication methods and printing techniques.

The asymmetrical anthra[2,3-b]benzo[d]thiophene unit has been previously prepared [4,5] and it was shown to have mobilities as high as 0.41 cm$^2$V$^{-1}$ s$^{-1}$.[4] The high mobility was achieved by preparation of the device at room temperature allowing the possible use of plastic flexible substrates. Furthermore, according to single-crystal X-ray diffraction studies, the anthra[2,3-b]benzo[d]thiophene unit exhibits a herringbone arrangement [4], which is similar to that of pentacene[6].

However, the herringbone arrangement reported for the anthra[2,3-b]benzo[d]thiophene unit is not optimal for charge transport in FET devices. Another disadvantage of anthra[2,3-b]benzo[d]thiophene as reported in prior art is that the material is only moderately soluble in common organic solvents, which means that the compound is not ideal for solution processing by mass-production printing techniques such as ink-jet, gravure and flexo printing.

However, prior art does neither disclose nor suggest how anthra[2,3-b]benzo[d]thiophene could be modified to improve its properties in the way described above. In particular, prior art does not provide any hint that this could be solved by adding subtituents to the anthra[2,3-b]benzo[d]thiophene core, or to the type or exact position of possible substituents.

SUMMARY OF THE INVENTION

The invention relates to compounds of formula I wherein

R$^1$ and R$^2$ are independently of each other halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl or germanyl groups, or optionally substituted carbyl or hydrocarbyl groups that optionally comprise one or more hetero atoms, R$^{3-6}$ are independently of each other H, halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl groups, or optionally substituted carbyl or hydrocarbyl groups that optionally comprise one or more hetero atoms, neighboured pairs of groups R$^3$ and R$^4$ or R$^5$ and R$^6$ may also form a ring system with each other or with the benzene ring to which they are attached, X$^0$ is halogen, R$^0$ and R$^{00}$ are independently of each other H or an optionally substituted aliphatic or aromatic hydrocarbyl group having 1 to 20 C atoms, and wherein the benzene rings may also be substituted by one or more additional groups R$^6$.

The invention further relates to a formulation comprising one or more compounds of formula I and one or more solvents, preferably selected from organic solvents.

The invention further relates to an organic semiconducting formulation comprising one or more compounds of formula I, one or more organic binders, or precursors thereof, preferably having a permittivity ∈ at 1,000 Hz of 3.3 or less, and optionally one or more solvents.

The invention further relates to the use of compounds and formulations according to the present invention as charge transport, semiconducting, electrically conducting, photoconducting or light emitting material in an optical, electrooptical, electronic, electroluminescent or photoluminescent components or devices.

The invention further relates to the use of compounds and formulations according to the present invention as charge transport, semiconducting, electrically conducting, photoconducting or light emitting material in optical, electrooptical, electronic, electroluminescent or photoluminescent components or devices.

The invention further relates to a charge transport, semiconducting, electrically conducting, photoconducting or light emitting material or component comprising one or more compounds or formulations according to the present invention.

The invention further relates to an optical, electrooptical or electronic component or device comprising one or more compounds, formulations, components or materials according to the present invention.

The optical, electrooptical, electronic electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

Figure 1:
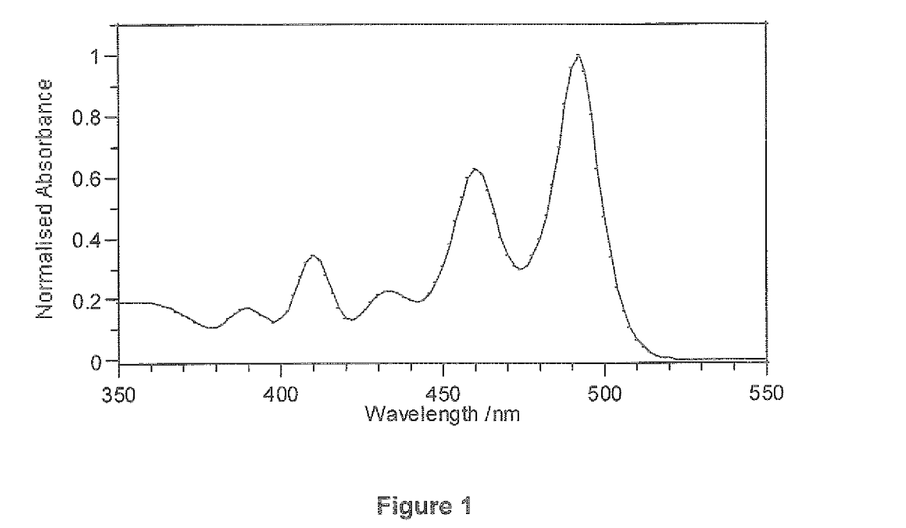
FIG. 1 shows the UV/V is absorption spectrum of 7,12-bis(triethylsilylethynyl)anthra[2,3-b]benzo[d]thiophene in DCM solution, with a maximum absorption wavelength $\lambda_{max}$=492 nm.
Figure 2:
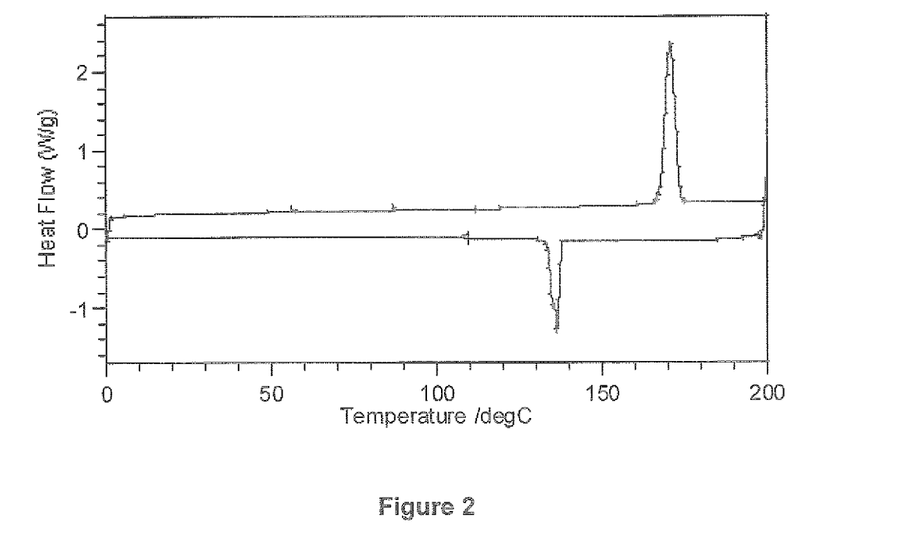
FIG. 2 shows the DSC curve (1$^{st}$ cycle) at 10° C./min for 7,12-bis(triethylsilylethynyl)anthra[2,3-b]benzo[d]thiophene, with a melting point T$_m$(onset)=168° C.
Figure 3:
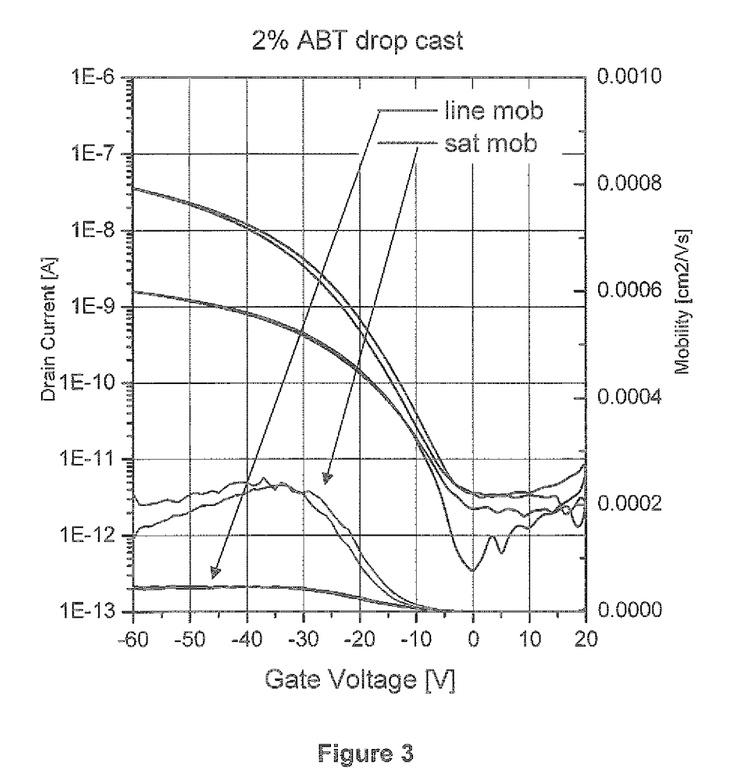
FIG. 3 shows the transfer characteristics and the charge carrier mobility of compound 1 in an organic field-effect transistor.

FIG. 1 and FIG. 2 show the UV vis spectrum and the DSC curve, respectively, of the compound prepared according to example 1.

DETAILED DESCRIPTION OF THE INVENTION

The anthra[2,3-b]benzo[d]thiophenes of the present invention are easy to synthesize and exhibit several advantageous properties, like a low bandgap, a high charge carrier mobility, a high solubility in organic solvents, a good processability for the device manufacture process, a high oxidative stability and a long lifetime in electronic devices. In addition, they show the following advantageous properties:

i) The addition of two ethynyl groups, preferably trialkylsilylethynyl groups, in 7- and 12 position of the anthra[2,3-b]benzo[d]thiophene core helps solubilising the molecular material in common organic solvents allowing the material to be easily solution processed. The addition of the (trialkylsilyl) ethynyl substituents also promotes the material to exhibit π-stacking order and thus to form highly organized crystalline films after deposition from solution.

ii) The size of the (trialkylsilyl)) ethynyl groups strongly influences the π-stacking interactions in the solid state. For small substituent groups, where the diameter of the trialkylsilyl group is significantly smaller than half the length of the scene core, a one-dimensional□π-stack or "slipped stack" arrangement is formed. However, when the size of the trialkylsilyl group is approximately the same as half the length of the acene core, a two-dimensional π-stack or "bricklayer" arrangement is favoured, which has been found to be the optimal for charge transport in FET devices. Therefore, by adding two trialkylsilyl groups of the correct size and in the correct position to the anthra[2,3-b]benzo[d]thiophene unit, the packing arrangement in the solid state is affected and a preferential π-stacking can be obtained with a suitably sized trialkylsilyl group.

iii) The HOMO energy level of trialkylsilylethynyl substituted anthra[2,3-b]benzo[d]thiophene is lower than that of anthra[2,3-b]benzo[d]thiophene due to the electron-withdrawing nature of the trialkylsilylethynyl groups. This enhances the oxidative stability of the material, which is particularly important for when it is applied as a semiconducting layer in an FET device. For reference, the HOMO energy level of the anthra[2,3-b]benzo[d]thiophene core is already measured as being 0.75 eV lower than that of pentacene.[4]

Especially preferred are compounds of formula I wherein one or more of R$^{3-6}$ denote aryl or heteroaryl optionally substituted by L, or straight chain, branched or cyclic alkyl with 1 to 20 C-atoms, which is unsubstituted or mono- or polysubstituted by F, Cl, Br or I, and wherein one or more non-adjacent CH$_2$ groups are optionally replaced, in each case independently from one another, by —O—, —S—, —NR$^0$—, —SiR$^0$R$^{00}$—, —CY$^1$=CY$^2$— or —C≡C— in such a manner that O and/or S atoms are not linked directly to one another, or denotes optionally substituted aryl or heteroaryl preferably having 1 to 30 C-atoms, with R$^0$ and R$^{00}$ being independently of each other H or alkyl with 1 to 12 C-atoms, Y$^1$ and Y$^2$ being independently of each other H, F, Cl or CN, and L being selected from F, Cl, Br, I, —CN, —NO$_2$, —NCO, —NCS, —OCN, —SCN, —C(=O)NR$^0$R$^{00}$, —C(=O)X$^0$, —C(=O)R$^0$, —NR$^0$R$^{00}$, optionally substituted silyl, or aryl or heteroaryl with 4 to 40, preferably 6 to 20 ring atoms, and straight chain or branched alkyl, alkoxy, oxaalkyl, thioalkyl, alkenyl, alkynyl, alkylcarbonyl, alkoxycarbonyl, alkylcarbonlyoxy or alkoxycarbonyloxy with 1 to 20, preferably 1 to 12 C atoms, wherein one or more H atoms are optionally replaced by F or Cl, wherein R$^0$, R$^{00}$ and X$^0$ are as defined above.

Further preferred are compounds of formula I wherein one or more groups R$^{3-6}$ are selected of formula -(A-B)$_a$-, wherein, in case of multiple occurrence independently of one another, A is selected from —CY$^1$=CY$^2$— or —C≡C— and B is selected from aryl or heteroaryl optionally substituted by L as defined above, with Y$^1$ and Y$^2$ being as defined above, and a being 1, 2 or 3.

Further preferred are compounds of formula I wherein one or more groups R$^{3-6}$ denote C$_1$-C$_{20}$-alkyl that is optionally substituted with one or more fluorine atoms, C$_1$-C$_{20}$-alkenyl, C$_1$-C$_{20}$-alkynyl, C$_1$-C$_{20}$-alkoxy or -oxaalkyl, C$_1$-C$_{20}$-thioalkyl, C$_1$-C$_{20}$-silyl, C$_1$-C$_{20}$-amino or C$_1$-C$_{20}$-fluoroalkyl, in particular from alkenyl, alkynyl, alkoxy, thioalkyl or fluoroalkyl, all of which are straight-chain and have 1 to 12, preferably 5 to 12 C-atoms, most preferably pentyl, hexyl, heptyl, octyl, nonyl, decyl, undecyl or dodecyl.

If two or more of the substituents R$^{3-6}$ form a ring system with each other and/or with the benzene ring to which they are attached, this is preferably a 5-, 6- or 7-membered aromatic or heteroaromatic ring, preferably selected from pyrrole, pyridine, pyrimidine, thiophene, selenophene, thiazole, thiadiazole, oxazole and oxadiazole, especially preferably thiophene or pyridine, all of which are optionally substituted by L as defined above.

Especially preferred are compounds of formula I, wherein one or both groups R$^1$ and R$^2$ denote a silyl group, or an optionally substituted aryl or heteroaryl group, preferably optionally substituted by L as defined above.

The silyl group is optionally substituted and is preferably selected of the formula -AR'R"R''', wherein A is Si or Ge, preferably Si, and R', R" and R''' are identical or different groups selected from H, a C$_1$-C$_{40}$-alkyl group, preferably C$_1$-C$_4$-alkyl, most preferably methyl, ethyl, n-propyl or isopropyl, a C$_2$-C$_{40}$-alkenyl group, preferably C$_2$-C$_7$-alkenyl, a C$_6$-C$_{40}$-aryl group, preferably phenyl, a C$_6$-C$_{40}$-arylalkyl group, a C$_1$-C$_{40}$-alkoxy or -oxaalkyl group, or a C$_6$-C$_{40}$-arylalkyloxy group, wherein all these groups are optionally substituted with one or more groups L as defined above. Preferably, R', R" and R''' are each independently selected from optionally substituted C$_{1-10}$-alkyl, more preferably C$_{1-4}$-alkyl, most preferably C$_{1-3}$-alkyl, for example isopropyl, and optionally substituted C$_{6-10}$-aryl, preferably phenyl. Further preferred is a silyl group wherein one or more of R', R" and R''' form a cyclic silyl alkyl group together with the Si or Ge atom, preferably having 1 to 8 C atoms.

In a preferred embodiment, R', R" and R''' are identical groups, for example identical, optionally substituted, alkyl groups, as in triisopropylsilyl. Very preferably the groups R', R" and R''' are identical, optionally substituted C$_{1-10}$, more preferably C$_{1-4}$, most preferably C$_{1-3}$ alkyl groups. A preferred alkyl group in this case is isopropyl.

A group of formula -AR'R"R''' or -AR'R"" as described above is a preferred optional substituent for the C$_1$-C$_{40}$-carbyl or hydrocarbyl group.

Preferred groups —SiR'R"R''' include, without limitation, trimethylsilyl, triethylsilyl, tripropylsilyl, dimethylethylsilyl, diethylmethylsilyl, dimethylpropylsilyl, dimethylisopropylsilyl, dipropylmethylsilyl, diisopropylmethylsilyl, dipropylethylsilyl, diisopropylethylsilyl, diethylisopropylsilyl, triisopropylsilyl, trimethoxysilyl, triethoxysilyl, trimethoxymethylsilyl, trivinylsilyl, triphenylsilyl, diphenylisopropylsilyl, diisopropylphenylsilyl, diphenylethylsilyl, diethylphenylsilyl, diphenylmethylsilyl, triphenoxysilyl, dimethylmethoxysilyl, dimethylphenoxysilyl, methylmethoxyphenylsilyl, etc., wherein the alkyl, aryl or alkoxy group is optionally substituted.

Especially preferred are the compounds of the following subformulae:

I1

I2

I3 wherein $R^{3-11}$, R', R" and R'" are as defined above, and $Y^3$, $Y^4$ and $Y^5$ are independently of each other selected from CH, $(CH)_2$, S, O, N and Se, such that S and/or O atoms are not directly linked to each other.

Especially preferred are compounds of formula I, I1 and I2 wherein $R^{3-6}$ denote H, F or alkyl or fluoroalkyl having from 1 to 12 C atoms, and/or $Y^3$—$Y^5$—$Y^4$ denotes CH—S—CH, CH—Se—CH, CH—O—CH, N—S—N, CH—N=CH or CH=N—CH, and/or R', R" and R'" denote $C_{1-10}$ alkyl.

The term "carbyl group" as used above and below denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term "hydrocarbyl group" denotes a carbyl group that does additionally contain one or more H atoms and optionally contains one or more hetero atoms like for example N, O, S, P, Si, Se, As, Te or Ge.

A carbyl or hydrocarbyl group comprising a chain of 3 or more C atoms may also be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ alkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_6$-$C_{12}$ aryl group and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

Aryl and heteroaryl preferably denote a mono-, bi- or tricyclic aromatic or heteroaromatic group with up to 25 C atoms that may also comprise condensed rings and is optionally substituted with one or more groups L as defined above.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

Especially preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, pyridine, preferably 2- or 3-pyridine, pyrimidine, thiophene preferably 2-thiophene, selenophene, preferably 2-selenophene, thieno[3,2-b]thiophene, thiazole, thiadiazole, oxazole and oxadiazole, especially preferably thiophene-2-yl, 5-substituted thiophene-2-yl or pyridine-3-yl, all of which can be unsubstituted, mono- or polysubstituted with L as defined above.

An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —CO—, these radicals are preferably neighboured. Accordingly these radicals together form a carbonyloxy group —CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxy-ethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —COO— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e. where one $CH_2$ group is replaced by —S—, is preferably straight-chain thiomethyl (—$SCH_3$), 1-thioethyl (—$SCH_2CH_3$), 1-thiopropyl —$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably straight-chain perfluoroalkyl $C_iF_{2i-1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

$R^{1-6}$ and R', R", R'" can be an achiral or a chiral group. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

—$CY^1$=$CY^2$— is preferably —CH=CH—, —CF=CF— or —CH=C(CN)—.

Halogen is F, Cl, Br or I, preferably F, Cl or Br.

The compounds of formula I may also be substituted with a polymerisable or reactive group, which is optionally protected during the process of forming the polymer. Particular preferred compounds of this type are those of formula I wherein one or more of $R^{3-6}$ or L denotes P-Sp, wherein P is a polymerisable or reactive group and Sp is a spacer group or a single bond. These compounds are particularly useful as semiconductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or reactive group P is selected from $CH_2$=$CW^1$—COO—, $CH_2$=$CW^1$—CO—, $CH_2$=$CW^2$—(O)$_{k1}$—, $CH_3$—CH=CH—O—, ($CH_2$=CH)$_2$CH—OCO—, ($CH_2$=CH—$CH_2$)$_2$CH—OCO—, ($CH_2$=CH)$_2$CH—O—, ($CH_2$=CH—$CH_2$)$_2$N—, ($CH_2$=CH—$CH_2$)$_2$N—CO—, HO—$CW^2W^3$—, HS—$CW^2W^3$—, $HW^2$N—, HO—$CW^2W^3$—NH—, $CH_2$=$CW^1$—CO—NH—, $CH_2$=CH—(COO)$_{k1}$-Phe-(O)$_{k2}$—, $CH_2$=CH—(CO)$_{k1}$-Phe-(O)$_{k2}$—, Phe-CH=CH—, HOOC—, OCN—, and $W^4W^5W^6$Si—, with $W^1$ being H, F, Cl, ON, $CF_3$, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, and $k_1$ and $k_2$ being independently of each other 0 or 1.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—COO—, $CH_2$=C($CH_3$)—COO—, $CH_2$=CH—, $CH_2$=CH—O—, ($CH_2$=CH)$_2$CH—OCO—, ($CH_2$=CH)$_2$CH—O—, or protected derivatives thereof.

Polymerisation of group P can be carried out according to methods that are known to the ordinary expert and described in the literature, for example in D. J. Broer; G. Challa; G. N. Mol, *Macromol. Chem,* 1991, 192, 59.

The term "spacer group" is known in prior art and suitable spacer groups Sp are known to the ordinary expert (see e.g. Pure Appl. Chem. 73(5), 888 (2001). The spacer group Sp is preferably of formula Sp'-X', such that P-Sp- is P-Sp'-XL, wherein Sp' is alkylene with up to 30 C atoms which is unsubstituted or mono- or polysubstituted by F, Cl, Br, I or CN, it being also possible for one or more non-adjacent CH$_2$ groups to be replaced, in each case independently from one another, by —O—, —S—, —NH—, —NR$^0$—, —CO—, —COO—, —OCO—, —OCO—O—, —S—CO—, —CO—S—, —CH=CH— or —C≡C— in such a manner that O and/or S atoms are not linked directly to one another, X' is —O—, —S—, —CO—, —COO—, —OCO—, —O—COO—, —CO—NR$^0$—, —NR$^0$—CO—, —NR$^0$—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond, R$^0$ and R$^{00}$ are independently of each other H or alkyl with 1 to 12 C-atoms, and Y$^1$ and Y$^2$ are independently of each other H, F, Cl or CN.

X' is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C— or a single bond, in particular —O—, —S—, —C≡C—, —CY$^1$=CY$^2$— or a single bond. In another preferred embodiment X' is a group that is able to form a conjugated system, such as —C≡C— or —CY$^1$=CY$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

The compounds of formula I can be synthesized according to or in analogy to methods that are known to the skilled person and are described in the literature. Other methods of preparation can be taken from the examples. Especially preferred and suitable synthesis methods are further described below.

The synthesis of the anthra[2,3-b]benzo[d]thiophene unit with added trialkylsilylethynyl groups is shown in Scheme 1. Commercially available dibenzothiophene undertakes a Friedel-Crafts reaction with phthalic anhydride to give 2-(2'-carboxybenzoyl)dibenzothiaphene. The acid is then treated with aluminum chloride and phosphorus pentachloride to yield anthra[2,3-b]benzo[d]thiophene-7,12-dione. The dione is alkylated with the lithium salt of the trialkylsilylacetylene reagent followed by aromatisation utilising tin (II) chloride under acidic conditions to give 7,12-bis(trialkylsilylethynyl) anthra[2,3-b]benzo[d]thiophene.

Scheme 1 wherein R is an alkyl group and wherein the bezene rings are optionally substituted with one or more groups $R^6$ as defined above and below.

The novel methods of preparing compounds as described above and below are another aspect of the invention. Especially preferred is a method of preparing a compound of formula I, comprising the following steps:

a) subjecting an optionally substituted dibenzothiophene to a Friedel-Crafts reaction with phthalic anhydride to give an optionally substituted 2-(2'-carboxybenzoyl) dibenzothiophene, b) treating the acid group of the product of step a) with a dehydrating agent, preferably aluminum chloride and phosphorus pentachloride, to give an optionally substituted anthra[2,3-b]benzo[d]thiophene-7,12-dione, c) reacting the product of step b) with the lithium salt of a trisubstituted silylacetylene reagent, preferably trialkylsilylacetylene, followed by aromatisation, preferably utilising tin (II) chloride, under acidic conditions to give 7,12-bis(trisubstituted silylethynyl)anthra[2,3-b]benzo[d]thiophene.

The invention further relates to a formulation comprising one or more compounds of formula I and one or more solvents, preferably selected from organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6fluorotoluene, 2-fluoroanisole, anisole, 2,3-dimethylpyrazine, fluoroanisole, 3-fluoroanisole, 3-trifluoro-methylanisole, 2-methylanisole, phenetol, 4-methylansiole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxybenzene, 1-methylnaphthalene, N-methylpyrrolidinone, 3-fluorobenzotrifluoride, benzotrifluoride, benzotrifluoride, dioxane, trifluoromethoxybenzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents with high boiling temperatures and solvent mixtures are preferred. For spin coating alkylated benzenes like xylene and toluene are preferred.

The invention further relates to an organic semiconducting formulation comprising one or more compounds of formula I, one or more organic binders, or precursors thereof, preferably having a permittivity $\in$ at 1,000 Hz of 3.3 or less, and optionally one or more solvents.

Combining specified soluble compounds of formula I, especially compounds of the preferred formulae as described above and below, with an organic binder resin (hereinafter also referred to as "the binder") results in little or no reduction in charge mobility of the compounds of formula I, even an increase in some instances. For instance, the compounds of formula I may be dissolved in a binder resin (for example poly(α-methylstyrene) and deposited (for example by spin coating), to form an organic semiconducting layer yielding a high charge mobility. Moreover, a semiconducting layer formed thereby exhibits excellent film forming characteristics and is particularly stable.

If an organic semiconducting layer formulation of high mobility is obtained by combining a compound of formula I with a binder, the resulting formulation leads to several advantages. For example, since the compounds of formula I are soluble they may be deposited in a liquid form, for example from solution. With the additional use of the binder the formulation can be coated onto a large area in a highly uniform manner. Furthermore, when a binder is used in the formulation it is possible to control the properties of the formulation to adjust to printing processes, for example viscosity, solid content, surface tension. Whilst not wishing to be bound by any particular theory it is also anticipated that the use of a binder in the formulation fills in volume between crystalline grains otherwise being void, making the organic semiconducting layer less sensitive to air and moisture. For example, layers formed according to the process of the present invention show very good stability in OFET devices in air.

The invention also provides an organic semiconducting layer which comprises the organic semiconducting layer formulation.

The invention further provides a process for preparing an organic semiconducting layer, said process comprising the following steps:

(i) depositing on a substrate a liquid layer of a formulation comprising one or more compounds of formula I as described above and below, one or more organic binder resins or precursors thereof, and optionally one or more solvents, (ii) forming from the liquid layer a solid layer which is the organic semiconducting layer, (iii) optionally removing the layer from the substrate.

The process is described in more detail below.

The invention additionally provides an electronic device comprising the said organic semiconducting layer. The electronic device may include, without limitation, an organic field effect transistor (OFET), organic light emitting diode (OLED), photodetector, sensor, logic circuit, memory element, capacitor or photovoltaic (PV) cell. For example, the active semiconductor channel between the drain and source in an OFET may comprise the layer of the invention. As another example, a charge (hole or electron) injection or transport layer in an OLED device may comprise the layer of the invention. The formulations according to the present invention and layers formed therefrom have particular utility in OFETs especially in relation to the preferred embodiments described herein.

The semiconducting compound of formula I preferably has a charge carrier mobility, μ, of more than 0.001 cm$^2$V$^{-1}$ s$^{-1}$, very preferably of more than 0.01 cm$^2$V$^{-1}$ s$^{-1}$, especially preferably of more than 0.1 cm$^2$V$^{-1}$ s$^{-1}$ and most preferably of more than 0.5 cm$^2$V$^{-1}$ s$^{-1}$.

The binder, which is typically a polymer, may comprise either an insulating binder or a semiconducting binder, or mixtures thereof may be referred to herein as the organic binder, the polymeric binder or simply the binder.

Preferred binders according to the present invention are materials of low permittivity, that is, those having a permittivity $\in$ at 1,000 Hz of 3.3 or less. The organic binder preferably has a permittivity $\in$ at 1,000 Hz of 3.0 or less, more preferably 2.9 or less. Preferably the organic binder has a permittivity $\in$ at 1,000 Hz of 1.7 or more. It is especially preferred that the permittivity of the binder is in the range from 2.0 to 2.9. Whilst not wishing to be bound by any particular theory it is believed that the use of binders with a permittivity $\in$ of greater than 3.3 at 1,000 Hz, may lead to a reduction in the OSC layer mobility in an electronic device, for example an OFET. In addition, high permittivity binders could also result in increased current hysteresis of the device, which is undesirable.

An example of a suitable organic binder is polystyrene. Further examples of suitable binders are disclosed for example in US 2007/0102696 A1. Especially suitable and preferred binders are described in the following.

In one type of preferred embodiment, the organic binder is one in which at least 95%, more preferably at least 98% and especially all of the atoms consist of hydrogen, fluorine and carbon atoms.

It is preferred that the binder normally contains conjugated bonds, especially conjugated double bonds and/or aromatic rings.

The binder should preferably be capable of forming a film, more preferably a flexible film. Polymers of styrene and α-methyl styrene, for example copolymers including styrene, α-methylstyrene and butadiene may suitably be used.

Binders of low permittivity of use in the present invention have few permanent dipoles which could otherwise lead to random fluctuations in molecular site energies. The permittivity $\in$ (dielectric constant) can be determined by the ASTM D150 test method.

It is also preferred that in the present invention binders are used which have solubility parameters with low polar and hydrogen bonding contributions as materials of this type have low permanent dipoles. A preferred range for the solubility parameters ('Hansen parameter') of a binder for use in accordance with the present invention is provided in Table 1 below.

TABLE 1

| | Hansen parameter | | |
|---|---|---|---|
| | $\delta_d$ MPa$^{1/2}$ | $\delta_p$ MPa$^{1/2}$ | $\delta_h$ MPa$^{1/2}$ |
| Preferred range | 14.5+ | 0-10 | 0-14 |
| More preferred range | 16+ | 0-9 | 0-12 |
| Most preferred range | 17+ | 0-8 | 0-10 |

The three dimensional solubility parameters listed above include: dispersive ($\delta_d$), polar ($\delta_p$) and hydrogen bonding ($\delta_h$) components (C. M. Hansen, Ind. Eng. and Chem., Prod. Res. and Devl., 9, No 3, p 282., 1970). These parameters may be determined empirically or calculated from known molar group contributions as described in Handbook of Solubility Parameters and Other Cohesion Parameters ed. A.F.M. Barton, CRC Press, 1991. The solubility parameters of many known polymers are also listed in this publication.

It is desirable that the permittivity of the binder has lithe dependence on frequency. This is typical of non-polar materials. Polymers and/or copolymers can be chosen as the binder by the permittivity of their substituent groups. A list of suitable and preferred low polarity binders is given (without limiting to these examples) in Table 2:

TABLE 2

| Binder | typical low frequency permittivity ($\epsilon$) |
|---|---|
| polystyrene | 2.5 |
| poly(α-methylstyrene) | 2.6 |

TABLE 2-continued

| Binder | typical low frequency permittivity ($\epsilon$) |
|---|---|
| poly(α-vinylnaphtalene) | 2.6 |
| poly(vinyltoluene) | 2.6 |
| polyethylene | 2.2-2.3 |
| cis-polybutadiene | 2.0 |
| polypropylene | 2.2 |
| polyisoprene | 2.3 |
| poly(4-methyl-1-pentene) | 2.1 |
| poly(4-methylstyrene) | 2.7 |
| poly(chorotrifluoroethylene) | 2.3-2.8 |
| poly(2-methyl-1,3-butadiene) | 2.4 |
| poly(p-xylylene) | 2.6 |
| poly(α-α-α'-α' tetrafluoro-p-xylylene) | 2.4 |
| poly[1,1-(2-methyl propane)bis(4-phenyl)carbonate] | 2.3 |
| poly(cyclohexyl methacrylate) | 2.5 |
| poly(chlorostyrene) | 2.6 |
| poly(2,6-dimethyl-1,4-phenylene ether) | 2.6 |
| polyisobutylene | 2.2 |
| poly(vinyl cyclohexane) | 2.2 |
| poly(vinylcinnamate) | 2.9 |
| poly(4-vinylbiphenyl) | 2.7 |

Other polymers suitable as binders include poly(1,3-butadiene) or polyphenylene.

Especially preferred are formulations wherein the binder is selected from poly-α-methyl styrene, polystyrene and polytriarylamine or any copolymers of these, and the solvent is selected from xylene(s), toluene, tetralin and cyclohexanone.

Copolymers containing the repeat units of the above polymers are also suitable as binders. Copolymers offer the possibility of improving compatibility with the compounds of formula I, modifying the morphology and/or the glass transition temperature of the final layer composition. It will be appreciated that in the above table certain materials are insoluble in commonly used solvents for preparing the layer. In these cases analogues can be used as copolymers. Some examples of copolymers are given in Table 3 (without limiting to these examples). Both random or block copolymers can be used. It is also possible to add some more polar monomer components as long as the overall composition remains low in polarity.

TABLE 3

| Binder | typical low frequency permittivity ($\epsilon$) |
|---|---|
| poly(ethylene/tetrafluoroethylene) | 2.6 |
| poly(ethylene/chlorotrifluoroethylene) | 2.3 |
| fluorinated ethylene/propylene copolymer | 2-2.5 |
| polystyrene-co-α-methylstyrene | 2.5-2.6 |
| ethylene/ethyl acrylate copolymer | 2.8 |
| poly(styrene/10% butadiene) | 2.6 |
| poly(styrene/15% butadiene) | 2.6 |
| poly(styrene/2,4 dimethylstyrene) | 2.5 |
| Topas ™ (all grades) | 2.2-2.3 |

Other copolymers may include: branched or non-branched polystyrene-block-polybutadiene, polystyrene-block(polyethylene-ran-butylene)-block-polystyrene, polystyrene-block-polybutadiene-block-polystyrene, polystyrene-(ethylene-propylene)-diblock-copolymers (e.g. KRATON®-G1701E, Shell), poly(propylene-co-ethylene) and poly(styrene-co-methylmethacrylate).

Preferred insulating binders for use in the organic semiconductor layer formulation according to the present invention are poly(α-methylstyrene), polyvinylcinnamate, poly(4-vinylbiphenyl), poly(4-methylstyrene), and Topas™ 8007 (linear olefin, cyclo-olefin(norbornene) copolymer available from Ticona, Germany). Most preferred insulating binders are poly(α-methylstyrene), polyvinylcinnamate and poly(4-vinylbiphenyl).

The binder can also be selected from crosslinkable binders, like e.g. acrylates, epoxies, vinylethers, thiolenes etc., preferably having a sufficiently low permittivity, very preferably of 3.3 or less. The binder can also be mesogenic or liquid crystalline.

As mentioned above the organic binder may itself be a semiconductor, in which case it will be referred to herein as a semiconducting binder. The semiconducting binder is still preferably a binder of low permittivity as herein defined. Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility, μ, of at least $10^{-5}$ $cm^2V^{-1}s^{-1}$, more preferably at least $10^{-4}$ $cm^2V^{-1}s^{-1}$.

A preferred class of semiconducting binder is a polymer as disclosed in U.S. Pat. No. 6,630,566, preferably an oligomer or polymer having repeat units of formula 1:

1 wherein
$Ar^1$, $Ar^2$ and $Ar^3$ which may be the same or different, denote, independently if in different repeat units, an optionally substituted aromatic group that is mononuclear or polynuclear, and
m is an integer ≥1, preferably ≥6, preferably ≥10, more preferably ≥15 and most preferably ≥20.

In the context of $Ar^1$, $Ar^2$ and $Ar^3$, a mononuclear aromatic group has only one aromatic ring, for example phenyl or phenylene. A polynuclear aromatic group has two or more aromatic rings which may be fused (for example napthyl or naphthylene), individually covalently linked (for example biphenyl) and/or a combination of both fused and individually linked aromatic rings. Preferably each $Ar^1$, $Ar^2$ and $Ar^3$ is an aromatic group which is substantially conjugated over substantially the whole group.

Further preferred classes of semiconducting binders are those containing substantially conjugated repeat units. The semiconducting binder polymer may be a homopolymer or copolymer (including a block-copolymer) of the general formula 2:

2 wherein A, B, . . . , Z each represent a monomer unit and (c), (d), . . . (z) each represent the mole fraction of the respective monomer unit in the polymer, that is each (c), (d), . . . (z) is a value from 0 to 1 and the total of (c)+(d)+ . . . +(z)=1.

Examples of suitable and preferred monomer units A, B, . . . Z include units of formula 1 above and of formulae 3 to 8 given below (wherein m is as defined in formula 1:

3 wherein
$R^a$ and $R^b$ are independently of each other selected from H, F, CN, $NO_2$, —N($R^c$)($R^d$) or optionally substituted alkyl, alkoxy, thioalkyl, acyl, aryl,

$R^c$ and $R^d$ are independently or each other selected from H, optionally substituted alkyl, aryl, alkoxy or polyalkoxy or other substituents, and wherein the asterisk (*) is any terminal or end capping group including H, and the alkyl and aryl groups are optionally fluorinated;

4 wherein
Y is Se, Te, O, S or —N($R^e$), preferably O, S or —N($R^e$)—,
$R^e$ is H, optionally substituted alkyl or aryl,
$R^a$ and $R^b$ are as defined in formula 3;

5 wherein $R^a$, $R^b$ and Y are as defined in formulae 3 and 4;

6 wherein $R^a$, $R^b$ and Y are as defined in formulae 3 and 4,
Z is —C($T^1$)=C($T^2$)-, —C≡C—, —N($R^f$)—, —N=N—, ($R^f$)=N—, —N=C($R^f$)—,
$T^1$ and $T^2$ independently of each other denote H, Cl, F, —CN or lower alkyl with 1 to 8 C atoms,
$R^f$ is H or optionally substituted alkyl or aryl;

7 wherein $R^a$ and $R^b$ are as defined in formula 3;

8 wherein $R^a$, $R^b$, $R^g$ and $R^h$ independently of each other have one of the meanings of $R^a$ and $R^b$ in formula 3.

In the case of the polymeric formulae described herein, such as formulae 1 to 8, the polymers may be terminated by any terminal group, that is any end-capping or leaving group, including H.

In the case of a block-copolymer, each monomer A, B, . . . Z may be a conjugated oligomer or polymer comprising a number, for example 2 to 50, of the units of formulae 3-8. The semiconducting binder preferably includes: arylamine, fluorene, thiophene, spiro bifluorene and/or optionally substituted aryl (for example phenylene) groups, more preferably arylamine, most preferably triarylamine groups. The aforementioned groups may be linked by further conjugating groups, for example vinylene.

In addition, it is preferred that the semiconducting binder comprises a polymer (either a homo-polymer or copolymer, including block-copolymer) containing one or more of the aforementioned arylamine, fluorene, thiophene and/or optionally substituted aryl groups. A preferred semiconducting binder comprises a homo-polymer or copolymer (including block-copolymer) containing arylamine (preferably triarylamine) and/or fluorene units. Another preferred semiconducting binder comprises a home-polymer or co-polymer (including block-copolymer) containing fluorene and/or thiophene units.

The semiconducting binder may also contain carbazole or stilbene repeat units. For example polyvinylcarbazole or polystilbene polymers or copolymers may be used. The semiconducting binder may optionally contain DBBDT segments (for example repeat units as described for formula 1 above) to improve compatibility with the soluble compounds of formula.

The most preferred semiconducting binders for use in the organic semiconductor layer formulation according to the present invention are poly(9-vinylcarbazole) and PTAA1, a polytriarylamine of the following formula wherein m is as defined in formula 1.

For application of the semiconducting layer in p-channel FETs, it is desirable that the semiconducting binder should have a higher ionisation potential than the semiconducting compound of formula I, otherwise the binder may form hole traps. In n-channel materials the semiconducting binder should have lower electron affinity than the n-type semiconductor to avoid electron trapping.

The formulation according to the present invention may be prepared by a process which comprises:
(i) first mixing a compound of formula I and an organic binder or a precursor thereof. Preferably the mixing comprises mixing the two components together in a solvent or solvent mixture,
(ii) applying the solvent(s) containing the compound of formula I and the organic binder to a substrate; and optionally evaporating the solvent(s) to form a solid organic semiconducting layer according to the present invention,
(iii) and optionally removing the solid layer from the substrate or the substrate from the solid layer.

In step (i) the solvent may be a single solvent or the compound of formula I and the organic binder may each be dissolved in a separate solvent followed by mixing the two resultant solutions to mix the compounds.

The binder may be formed in situ by mixing or dissolving a compound of formula I in a precursor of a binder, for example a liquid monomer, oligomer or crosslinkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer. If a preformed binder is used it may be dissolved together with the compound of formula I in a suitable solvent, and the solution deposited for example by dipping, spraying, painting or printing it on a substrate to form a liquid layer and then removing the solvent to leave a solid layer. It will be appreciated that solvents are chosen which are able to dissolve both the binder and the compound of formula I, and which upon evaporation from the solution blend give a coherent defect free layer.

Suitable solvents for the binder or the compound of formula I can be determined by preparing a contour diagram for the material as described in ASTM Method D 3132 at the concentration at which the mixture will be employed. The material is added to a wide variety of solvents as described in the ASTM method.

It will also be appreciated that in accordance with the present invention the formulation may also comprise two or more compounds of formula I and/or two or more binders or binder precursors, and that the process for preparing the formulation may be applied to such formulations.

Examples of suitable and preferred organic solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetralin, decalin, indane and/or mixtures thereof.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 38, No 496, 296 (1966)". Solvent blends may also be used and can be identified as described in "Solvents, W. H. Ellis, Federation of Societies for Coatings Technology, p 9-10, 1986". Such a procedure may lead to a blend of 'non' solvents that will dissolve both the binder and the compound of formula I, although it is desirable to have at least one true solvent in a blend.

Especially preferred solvents for use in the formulation according to the present invention, with insulating or semiconducting binders and mixtures thereof, are xylene(s), toluene, tetralin and o-dichlorobenzene.

The proportions of binder to the compound of formula I in the formulation or layer according to the present invention are typically 20:1 to 1:20 by weight, preferably 10:1 to 1:10 more preferably 5:1 to 1:5, still more preferably 3:1 to 1:3 further preferably 2:1 to 1:2 and especially 1:1. Surprisingly and beneficially, dilution of the compound of formula I in the binder has been found to have little or no detrimental effect on the charge mobility, in contrast to what would have been expected from the prior art.

In accordance with the present invention it has further been found that the level of the solids content in the organic semiconducting layer formulation is also a factor in achieving improved mobility values for electronic devices such as OFETs. The solids content of the formulation is commonly expressed as follows:

$$\text{Solids content (\%)} = \frac{a+b}{a+b+c} \times 100$$

wherein
a=mass of compound of formula I, b=mass of binder and c=mass of solvent.

The solids content of the formulation is preferably 0.1 to 10% by weight, more preferably 0.5 to 5% by weight.

Surprisingly and beneficially, dilution of the compound of formula I in the binder has been found to have little or no effect on the charge mobility, in contrast to what would have been expected from the prior art.

The compounds according to the present invention can also be used in mixtures or blends, for example together with other compounds having charge-transport, semiconducting, electrically conducting, photoconducting and/or light emitting semiconducting properties. Thus, another aspect of the invention relates to a mixture or blend comprising one or more compounds of formula I and one or more further compounds having one or more of the above-mentioned properties. These mixtures can be prepared by conventional methods that are described in prior art and known to the skilled person. Typically the compounds are mixed with each other or dissolved in suitable solvents and the solutions combined.

The formulations according to the present invention can additionally comprise one or more further components like for example surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

It is desirable to generate small structures in modern microelectronics to reduce cost (more devices/unit area), and power consumption. Patterning of the layer of the invention may be carried out by photolithography or electron beam lithography.

Liquid coating of organic electronic devices such as field effect transistors is more desirable than vacuum deposition techniques. The formulations of the present invention enable the use of a number of liquid coating techniques. The organic semiconductor layer may be incorporated into the final device structure by, for example and without limitation, dip coating, spin coating, ink jet printing, letter-press printing, screen printing, doctor blade coating, roller printing, reverse-roller printing, offset lithography printing, flexographic printing, web printing, spray coating, brush coating or pad printing. The present invention is particularly suitable for use in spin coating the organic semiconductor layer into the final device structure.

Selected formulations of the present invention may be applied to prefabricated device substrates by ink jet printing or microdispensing. Preferably industrial piezoelectric print heads such as but not limited to those supplied by Aprion, Hitachi-koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the mixture of the compound of formula I and the binder should be first dissolved in a suitable solvent. Solvents must fulfill the requirements stated above and must not have any detrimental effect on the chosen print head. Additionally, solvents should have boiling points >100° C., preferably >140° C. and more preferably >150° C. in order to prevent operability problems caused by the solution drying out inside the print head. Suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a formulation according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the binder and the compound of formula I which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1 to 100 mPa·s, more preferably 1 to 50 mPa·s and most preferably 1 to 30 mPa·s.

The use of the binder in the present invention also allows the viscosity of the coating solution to be tuned to meet the requirements of the particular print head.

The semiconducting layer of the present invention is typically at most 1 micron (=1 μm) thick, although it may be thicker if required. The exact thickness of the layer will depend, for example, upon the requirements of the electronic device in which the layer is used. For use in an OFET or OLED, the layer thickness may typically be 500 nm or less.

In the semiconducting layer of the present invention there may be used two or more different compounds of formula I. Additionally or alternatively, in the semiconducting layer there may be used two or more organic binders of the present invention.

As mentioned above, the invention further provides a process for preparing the organic semiconducting layer which comprises (i) depositing on a substrate a liquid layer of a formulation which comprises one or more compounds of formula I, one or more organic binders or precursors thereof and optionally one or more solvents, and (ii) forming from the liquid layer a solid layer which is the organic semiconducting layer.

In the process, the solid layer may be formed by evaporation of the solvent and/or by reacting the binder resin precursor (if present) to form the binder resin in situ. The substrate may include any underlying device layer, electrode or separate substrate such as silicon wafer or polymer substrate for example.

In a particular embodiment of the present invention, the binder may be alignable, for example capable of forming a liquid crystalline phase. In that case the binder may assist alignment of the compound of formula I, for example such that their aromatic core is preferentially aligned along the direction of charge transport. Suitable processes for aligning the binder include those processes used to align polymeric organic semiconductors and are described in prior art, for example in US 2004/0248338 A1.

The formulation according to the present invention can additionally comprise one or more further components like for example surface-active compounds, lubricating agents, wetting agents, dispersing agents, hydrophobing agents, adhesive agents, flow improvers, defoaming agents, deaerators, diluents, reactive or non-reactive diluents, auxiliaries, colourants, dyes or pigments, furthermore, especially in case crosslinkable binders are used, catalysts, sensitizers, stabilizers, inhibitors, chain-transfer agents or co-reacting monomers.

The present invention also provides the use of the semiconducting compound, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising the formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The compounds and formulations according to the present invention are useful as charge transport, semiconducting, electrically conducting, photoconducting or light emitting materials in optical, electrooptical, electronic, electroluminescent or photoluminescent components or devices. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns. In these devices, the compounds of the present invention are typically applied as thin layers or films.

For example, the compound or formulation may be used as a layer or film, in a field effect transistor (FET) for example as the semiconducting channel, organic light emitting diode (OLED) for example as a hole or electron injection or transport layer or electroluminescent layer, photodetector, chemical detector, photovoltaic cell (PVs), capacitor sensor, logic circuit, display, memory device and the like. The compound or formulation may also be used in electrophotographic (EP) apparatus.

The compound or formulation is preferably solution coated to form a layer or film in the aforementioned devices or apparatus to provide advantages in cost and versatility of manufacture. The improved charge carrier mobility of the compound or formulation of the present invention enables such devices or apparatus to operate faster and/or more efficiently.

The compound, formulation and layer of the present invention are especially suitable for use in an organic field effect transistor OFET as the semiconducting channel. Accordingly, the invention also provides an organic field effect transistor (OFET) comprising a gate electrode, an insulating (or gate insulator) layer, a source electrode, a drain electrode and an organic semiconducting channel connecting the source and drain electrodes, wherein the organic semiconducting channel comprises an organic semiconducting layer according to the present invention. Other features of the OFET are well known to those skilled in the art.

OFETs where an organic semiconducting (OSC) material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
a source electrode,
a drain electrode,
a gate electrode,
a semiconducting layer,
one or more gate insulator layers,
optionally a substrate.
wherein the semiconductor layer preferably comprises a compound of formula I, very preferably a formulation comprising a compound of formula I and an organic binder as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric constant) from 1.0 to 5.0, very preferably from 1.8 to 4.0 ("low k materials"), as disclosed for example in US 2007/0102696 A1 or U.S. Pat. No. 7,095,044.

An OPV device according to the present invention preferably comprises:
- a low work function electrode (for example Aluminum),
- a high work function electrode (for example ITO), one of which is transparent,
- a bilayer of consisting of a hole transporting and an electron transporting material; the bilayer can exist as two distinct layers, or as a blended mixture, a so-called bulk heterjunction (BHJ) (see for example Coakley, K. M. and McGehee, M. D. Chem. Mater. 2004, 16, 4533),
- an optional conducting polymer layer (such as for example PEDOT:PSS) to modify the work function of the high work function electrode to provide an ohmic contact for the hole,
- an optional coating on the high workfunction electrode (such as LiF) to provide an ohmic contact for electrons.

The hole transporting material is constituted by a compound of the present invention. The electron transporting material can be an inorganic material such as zinc oxide or cadmium selenide, or an organic material such as a fullerene derivate (for example PCBM, [(6,6)-phenyl C61-butyric acid methyl ester] or a polymer see for example Coakley, K. M. and McGehee, M. D. Chem. Mater. 2004, 16, 4533). For the blended mixture, an optional annealing step may be necessary to optimize blend morpohology and consequently OPV device performance.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention can be used in organic light emitting devices or diodes (OLEDs), e.g., in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the materials according to the present invention, especially those which show photoluminescent properties, may be employed as materials of light sources, e.g., of display devices such as described in EP 0 889 350 A1 or by C. Weder et al., Science, 279, 1998, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, La$(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention may also be suitable for use in organic plasmon-emitting diodes (OPEDs), as described for example in Koller et al., Nature Photonics 2008 (published online Sep. 28, 2008).

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film.

The materials according to the present invention may also be combined with photoisomerisable compounds and/or chromophores for use in or as photoalignment layers, as described in US 2003/0021913.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, Proc. Natl. Acad. Sci. U.S.A. 1999, 96, 12287; D. Wang, X. Gong, P. S. Heeger, F. Rininsland, G. C. Bazan and A. J. Heeger, Proc. Natl. Acad. Sci. U.S.A. 2002, 99, 49; N. DiCesare, M. R. Pinot, K. S. Schanze and J. R. Lakowicz, Langmuir 2002, 18, 7785; D. T. McQuade, A. E. Pullen, T. M. Swager, Chem. Rev. 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

REFERENCES

1. J. E. Anthony, *Angew. Chem. Int. Ed.*, 2008, 47, 452.
2. S. F. Nelson, Y. Y. Lin, D. J. Gundlach and T. N. Jackson, *Appl. Phys. Lett.*, 1998, 72, 1854.
3. Maliakal, K. Raghavachari, H. Katz, E. Chandross and T. Siegrist, *Chem. Mater.*, 2004, 16, 4980.
4. Du, Y. Guo, Y. Liu, W. Qiu, H. Zhang, X. Gao, Y. Liu, T. Qi, K. Lu and G. Yu, *Chem. Mater.*, 2008, 20 (13), 4188.
5. M. L. Tedjamulia, Y. Tominaga and R. N. Castle, *J. Heterocyclic Chem.*, 1983, 20, 861. (b) F. Mayer, *Ann. Chem.*, 488, 259.
6. S. T. Bromley, M. Mas-Torrent, P. Hadley and C. Rovira, *J. Am. Chem. Soc.*, 2004, 126, 6544.
7. M. L. Tang, M. E. Roberts, J. J. Lacklin, M. M. Ling, H. Meng and Z. Bao, *Chem. Mater.*, 2006, 18, 6250.

The invention will now be described in more detail by reference to the following examples, which are illustrative only and do not limit the scope of the invention.

Example 1

7,12-Bis(triethylsilylethynyl)anthra[2,3-b]benzo[d]thiophene 1 is Prepared in Three Steps as Follows 2-o-Carboxybenzoyl)dibenzothiophene To a mixture of aluminum chloride (40.0 g, 300 mmol) in anhydrous dichloromethane (1000 cm$^3$) is added a suspension of phthalic anhydride (14.8 g, 100 mmol) in anhydrous dichloromethane (200 cm$^3$). The suspension is stirred for 30 minutes, cooled to 5° C. and then a solution of dibenzothiophene (20.0 g, 110 mmol) in anhydrous dichloromethane (200 cm$^3$) added drop wise under cooling with ice. After addition, the mixture is allowed to stir at 23° C. for 4 hours. The reaction mixture poured into a solution of water (1000 cm$^3$) and concentrated hydrochloric acid (400 cm$^3$). The product extracted with dichloromethane (2 200 cm$^3$) and the organic extracted with aqueous sodium hydroxide (5%, 500 cm$^3$). The basic layer acidified and the oily precipitate is isolated by decanting away the acidic solution. Water (200 cm$^3$) is added, which solidified the oil and the solid collected by filtration, washed with water (500 cm$^3$) and dried under vacuum to give 2-(o-carboxybenzoyl)dibenzothiophene as a pale yellow solid (35.64 g, 99%). $^1$H NMR (300 MHz, CDCl$_3$) 8.47-8.52 (m, 1H), 7.99-8.15 (m, 2H), 7.60-7.86 (m, 4H), 7.35-7.57 (m, 4H).

Anthra[2,3-b]benzo[d]thiophene-7,12-dione

To a mixture of 2-(o-carboxybenzoyl)dibenzothiophene (35.6 g, 107 mmol) and phosphorus pentachloride (33.5 g, 161 mmol) in anhydrous 1,2-dichlorobenzene (430 cm$^3$) is added aluminum chloride (21.4 g, 161 mmol). The mixture is then heated at 140° C. for 17 hours. The reaction mixture cooled to 23° C. and the solvent removed under vacuum to give a black solid. Acetone (500 cm$^3$) is added and the mixture filtered to give a green/yellow solid which is dried under vacuum. To the solid is added dichloromethane (1000 cm$^3$) and the mixture heated. The hot mixture is passed through a very short plug of silica (dichloromethane) to give anthra[2,3-b]benzo[d]thiophene-7,12-dione as a yellow solid (5.43 g, 16%). MS m/z 314 (M$^+$). $^1$H NMR (300 MHz, CDCl$_3$) 9.04 (s, 1H), 8.73 (s, 1H), 8.31-8.41 (m, 3H), 7.86-7.93 (m, 1H), 7.78-7.85 (m, 2H), 7.50-7.61 (m, 2H); $^{13}$C NMR (75 MHz, CDCl$_3$) 183.1, 182.8, 145.3, 141.3, 139.9, 134.7, 134.2, 134.1, 133.9, 133.8, 131.1, 129.9, 128.8, 127.4, 125.5, 123.2, 123.1, 122.4, 120.8.

7,12-Bis(triethylsilylethynyl)anthra[2,3-b]benzo[d]thiophene 1

To a solution of triethylsilyl acetylene (3.68 g, 25 mmol) in anhydrous 1,4-dioxane (120 cm$^3$) at room temperature is added n-butyllithium (2.5 M in hexanes, 9.7 cm³, 24 mmol) dropwise. The reaction mixture is then stirred for 1 hour at 23° C. before anthra[2,3-b]benzo[d]thlophene-7,12-dione (2.00 g, 6.36 mmol) is added. The reaction mixture is then heated at reflux for 6 hours, the heating turned off and the mixture allowed to cool in the dark. Solid tin(II) chloride (8.93 g, 47 mmol) is added piecewise over 5 minutes and then the reaction mixture allowed to stir for a further 5 minutes. Concentrated hydrochloric acid (20 cm³) added slowly, and the mixture stirred for 1 hour in the dark. The mixture poured into water (200 cm³) and the product extracted with dichloromethane (2 100 cm³). The combined organic extracts dried over anhydrous magnesium sulfate, filtered and the solvent removed in vacuo to give a brown/purple solid. The crude product is purified by column chromatography (40-60 petrol to 10% dichloromethane in petrol) followed by recrystallisation from 2-butanone to give 7,12-bis(triethylsilylethynyl)anthra[2,3-b]benzo[d]thiophene 1 as an orange/red crystalline solid (740 mg, 21%). $^1$H NMR (300 MHz, CDCl$_3$) 9.39 (d, 1H, J 0.76), 9.02 (d, 1H, J 0.76), 8.58-8.67 (m, 2H), 8.18-8.25 (m, 1H), 7.73-7.49 (m, 1H), 7.57-7.64 (m, 2H), 7.43-7.49 (m, 2H), 1.19-1.32 (m, 18H), 0.84-0.97 (m, 12H); $^{13}$C NMR (75 MHz, CDCl$_3$) 140.6, 139.4, 136.5, 134.9, 132.5, 131.9, 131.2, 129.9, 128.5, 127.3, 127.0, 126.6, 124.8, 122.9, 122.2, 119.8, 119.4, 119.0, 117.2, 106.5, 106.2, 103.0, 102.9, 8.0, 7.9, 4.8, 4.7.

Example 2

Transistor Fabrication and Measurement

Top-gate thin-film organic field-effect transistors (OFETs) were fabricated on glass substrates with photolithographically defined Au source-drain electrodes. A 2 wt. % solution of compound 1 in a mixture of 4-methylanisole: 1-methyl-naphthalene (97:3) was drop-cast ontop followed by a spin-coated fluoropolymer dielectric material (D139). Finally a photolithographically defined Au gate electrode was deposited. The electrical characterization of the transistor devices was carried out in ambient air atmosphere using computer controlled Agilent 4155C Semiconductor Parameter Analyser. Charge carrier mobility in the saturation regime ($\mu_{sat}$) of 2×10$^{-4}$ cm²/Vs was calculated for compound 1 and a current on/off ratio of 1×10$^3$ was observed. Field-effect mobility was calculated in the saturation regime (V$_d$>(V$_g$-V$_0$)) using equation (1):

$$\left(\frac{dI_d^{sat}}{dV_g}\right)_{V_d} = \frac{WC_i}{L}\mu^{sat}(V_g - V_0) \quad (1)$$

where W is the channel width, L the channel length, $C_i$ the capacitance of insulating layer, $V_g$ the gate voltage, $V_0$ the turn-on voltage, and $\mu_{sat}$ is the charge carrier mobility in the saturation regime. Turn-on voltage (V$_0$) was determined as the onset of source-drain current.

The invention claimed is:
1. A compound of formula I wherein
R$^1$ and R$^2$ are independently of each other halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, an optionally substituted silyl or germanyl group, or an optionally substituted carbyl or hydrocarbyl group that optionally comprises one or more hetero atoms,
R$^{3-6}$ are independently of each other H, halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, an optionally substituted silyl group, or an optionally substituted carbyl or hydrocarbyl group that optionally comprise one or more hetero atoms, wherein a pair of groups R$^3$ and R$^4$ or R$^5$ and R$^6$ optionally form a ring system with each other or with the benzene ring to which they are attached,
X$^0$ is halogen,
R$^0$ and R$^{00}$ are independently of each other H or an optionally substituted aliphatic or aromatic hydrocarbyl group having 1 to 20 C atoms,
and wherein the benzene rings are optionally substituted by one or more additional groups R$^6$.
2. A compound according to claim 1, which is of formula I1, I2, I3 or I4 wherein

R³⁻¹¹ are independently of each other H, halogen, —CN, —NC, —NCO, —NCS, —OCN, —SCN, —C(═O)NR⁰R⁰⁰, —C(═O)X⁰, —C(═O)R⁰, —NH₂, —NR⁰R⁰⁰, —SH, —SR⁰, —SO₃H, —SO₂R⁰, —OH, —NO₂, —CF₃, —SF₅, an optionally substituted silyl group, or an optionally substituted carbyl or hydrocarbyl group that optionally comprise one or more hetero atoms, wherein a pair of groups R³ and R⁴ or R⁵ and R⁶ optionally form a ring system with each other or with the benzene ring to which they are attached, R', R" and R'" are independently of each other H, a C₁-C₄₀-alkyl group, a C₂-C₄₀-alkenyl group, a C₆-C₄₀-aryl group, a C₆-C₄₀-arylalkyl group, a C₁-C₄₀-alkoxy or -oxaalkyl group, or a C₆-C₄₀-arylalkyloxy group, each of which is optionally substituted with one or more L, L is F, Cl, Br, I, —CN, —NO₂, —NCO, —NCS, —OCN, —SCN, —C(═O)NR⁰R⁰⁰, —C(═O)X⁰, —C(═O)R⁰, —NR⁰R⁰⁰, optionally substituted silyl, or aryl or heteroaryl with 4 to 40 ring atoms, or straight chain or branched alkyl, alkoxy, oxaalkyl, thioalkyl, alkenyl, alkynyl, alkylcarbonyl, alkoxycarbonyl, alkylcarbonyloxy or alkoxycarbonyloxy with 1 to 20 C atoms, wherein one or more H atoms are optionally replaced by F or Cl, R⁰, R⁰⁰ are independently of each other H or an optionally substituted aliphatic or aromatic hydrocarbyl group having 1 to 20 C atoms, X⁰ is halogen, Y³, Y⁴ and Y⁵ are independently of each other CH, (CH)₂, S, O, N or Se, such that S and/or O atoms are not directly linked to each other.

3. A compound according to claim 2, wherein

R³⁻⁶ denote H, F or alkyl or fluoroalkyl having from 1 to 12 C atoms,

Y³, Y⁴ and Y⁵ denote CH—S—CH, CH—Se—CH, CH—O—CH, N—S—N, CH—N═CH or CH═N—CH, and

R', R" and R'" denote C₁₋₁₀ alkyl.

4. A compound according to claim 3, which is of formula I1.

5. A compound according to claim 3, which is of formula I2.

6. A compound according to claim 3, which is of formula I3.

7. A compound according to claim 2, wherein

R³⁻¹¹ are independently of each other H, halogen, —CN, —NC, —NCO, —NCS, —OCN, —SCN, —C(═O)NR⁰R⁰⁰, —C(═O)X⁰, —C(═O)R⁰, —NH₂, —NR⁰R⁰⁰, —SH, —SR⁰, —SO₃H, —SO₂R⁰, —OH, —NO₂, —CF₃, —SF₅, a silyl group, or a carbyl or hydrocarbyl group that optionally comprise one or more hetero atoms, wherein a pair of groups R³ and R⁴ or R⁵ and R⁶ optionally form a ring system with each other or with the benzene ring to which they are attached, L is F, Cl, Br, I, —CN, —NO₂, —NCO, —NCS, —OCN, —SCN, —C(═O)NR⁰R⁰⁰, —C(═O)X⁰, —C(═O)R⁰, —NR⁰R⁰⁰, silyl, or aryl or heteroaryl with 4 to 40 ring atoms, or straight chain or branched alkyl, alkoxy, oxaalkyl, thioalkyl, alkenyl, alkynyl, alkylcarbonyl, alkoxycarbonyl, alkylcarbonlyoxy or alkoxycarbonyloxy with 1 to 20 C atoms, wherein one or more H atoms are optionally replaced by F or Cl, R⁰, R⁰⁰ are independently of each other H or an aliphatic or aromatic hydrocarbyl group having 1 to 20 C atoms.

8. A compound according to claim 2, which is of formula I1, I2 or I3.

9. A composition comprising one or more compounds according to claim 1 and one or more organic solvents.

10. An organic semiconducting composition comprising one or more compounds according to claim 1, one or more organic binders or precursors thereof, having a permittivity ∈ at 1,000 Hz of 3.3 or less, and optionally one or more solvents.

11. A charge transport, semiconducting, electrically conducting, photoconducting or light emitting material in an optical, electrooptical, electronic, electroluminescent or photoluminescent component or device, comprising a compound according to claim 1.

12. A charge transport, semiconducting, electrically conducting, photoconducting or light emitting material or component comprising one or more compounds according to claim 1.

13. An optical, electrooptical, electronic, electroluminescent or photoluminescent component or device comprising one or more compounds according to claim 1.

14. A component or device according to claim 13, which is selected from the group consisting of organic field effect transistors (OFET), thin film transistors (TFT), integrated circuits (IC), logic circuits, capacitors, radio frequency identification (RFID) tags, radio frequency identification (RFID) devices radio frequency identification (RFID) components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers in polymer light emitting diodes (PLEDs), interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, components for detecting and discriminating DNA sequences, and devices for detecting and discriminating DNA sequences.

15. A method for preparing a compound according to claim 1, comprising:
   a) subjecting an optionally substituted dibenzothiophene to a Friedel-Crafts reaction with phthalic anhydride to give an optionally substituted 2-(2'-carboxybenzoyl)dibenzothiophene,
   b) treating the acid group of the product of step a) with a dehydrating agent, to give an optionally substituted anthra[2,3-b]benzo[d]thiophene-7,12-dione,
   c) reacting the product of step b) with the lithium salt of a trisubstituted silylacetylene reagent, followed by aromatisation, optionally by tin (II) chloride, under acidic conditions to give 7,12-bis(trisubstituted silylethynyl)anthra[2,3-b]benzo[d]thiophene.

16. A compound according to claim 1, wherein $R^1$ and $R^2$ are independently of each other halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, a silyl or germanyl group, or a carbyl or hydrocarbyl group that optionally comprises one or more hetero atoms, $R^{3-6}$ are independently of each other H, halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, a silyl group, or a carbyl or hydrocarbyl group that optionally comprise one or more hetero atoms, wherein a pair of groups $R^3$ and $R^4$ or $R^5$ and $R^6$ optionally form a ring system with each other or with the benzene ring to which they are attached, $R^0$ and $R^{00}$ are independently of each other H or an aliphatic or aromatic hydrocarbyl group having 1 to 20 C atoms.

17. A compound according to claim 1, which is 7,12-Bis(triethylsilylethynyl)anthra[2,3-b]benzo[d]thiophene.

* * * * *